United States Patent [19]
Feinstein et al.

[11] 3,935,265
[45] Jan. 27, 1976

[54] VAPOR PHASE CONVERSION OF AROMATIC ESTERS TO AROMATIC ALDEHYDES

[75] Inventors: Allen Feinstein, Wheaton; Ellis K. Fields, River Forest, both of Ill.

[73] Assignee: Standard Oil Company, Chicago, Ill.

[22] Filed: May 9, 1974

[21] Appl. No.: 468,429

[52] U.S. Cl........ 260/599; 260/668 R; 260/476 R; 260/469; 260/600 R; 260/465 R
[51] Int. Cl.$^2$.......................................... C07C 45/00
[58] Field of Search............ 260/599, 600 R, 476 R, 260/668 R, 469, 465 R

[56] References Cited
FOREIGN PATENTS OR APPLICATIONS
102,791  10/1962  Netherlands........................ 260/599

*Primary Examiner*—Bernard Helfin
*Attorney, Agent, or Firm*—William C. Clarke; Arthur G. Gilkes; William T. McClain

[57] ABSTRACT

A process for converting an aromatic methyl ester (methyl benzoate) to a corresponding aromatic aldehyde (benzaldehyde) by subjecting the ester to temperatures of 400° to 500°C and one atmosphere pressure for 3 to 100 seconds in the presence of a solid alumina catalyst.

5 Claims, No Drawings

VAPOR PHASE CONVERSION OF AROMATIC ESTERS TO AROMATIC ALDEHYDES

BACKGROUND OF THE INVENTION

The field of this invention relates to a new vapor phase catalytic conversion of aromatic esters to aromatic aldehydes. As literature reports, previous attempts to prepare aromatic adlehydes directly from aromatic esters involve the use of complex metal reducing agents such as sodium aluminum hydride (Zakharkin, L. I., Garrilenko, V. V., Maslin, D. N., and Khorlina, I. M., *Tetrahedron Lett.*, 29, 2087 (1963)), sodium bis(2-methoxyethoxy) aluminum hydride (Vit., J., *Org. Chem. Bull.*, 42, 1 (1970)), and diisobutylaluminum dihydride (Zakharkin, L. I., and Khorlina, I. M., *Tetrahedron Lett.*, 14, 619 (1962)). These reductions require long reaction times (5 to 7 hours) and temperatures ranging from −45° to −70°C. High yields of aromatic aldehydes are generally not achieved, as the aldehyde undergoes a Tishchenko-type condensation catalyzed by the metal reducing agent (Zakharkin, L. I., and Sorokina, L. P., *Zh. Obshch. Khim.*, 37, 561 (1967)).

In contrast to this, we have discovered that when an aromatic ester, wherein the portion of the ester group derived from the alcohol has no β-hydrogens, is heated in the vapor phase to a temperature in excess of 400°C and is passed over an alumina catalyst at essentially ambient pressure for as short a time as 3 seconds, the corresponding aromatic aldehyde will be produced as the dominant product.

SUMMARY OF THE INVENTION

We have discovered a new method of converting an aromatic ester, wherein the alkyl radical of said aromatic ester is free of β-hydrogens, to an aromatic aldehyde by contacting the aromatic ester with alumina at from about 400° to 500°C. The chemical reaction of our invention is categorically a vapor-phase heterogeneous catalysis which can be performed at atmospheric pressure.

In one aspect of our invention, methyl benzoate is decomposed by passing over alumina at 400° to 500°C and atmospheric pressure to give benzaldehyde as a major product. Other products formed include benzene, toluene and benzyl benzoate. In another aspect of our invention, substituted methyl benzoates are catalytically decomposed by passing over alumina to yield the corresponding substituted benzaldehydes (in a stereospecific manner) as major products. Other aspects of our invention will be apparent to one skilled in this art upon complete reading of the specification and examples.

DESCRIPTION OF THE INVENTION

The novel vapor-phase catalytic conversion of a carbomethoxy group of an aromatic ester to the aldehyde can perhaps be best understood by examining the specific embodiment involving the conversion of methyl benzoate to benzaldehyde. Although the chemistry may not be fully known, a reaction mechanism can be proposed which is consistent with the observed experimental data. Further, it is felt that the experimental observations categorically support a hydrogen abstraction step rather than mere thermal degradation presently found in literature. However, any proposed mechanism (specifically our proposed mechanism) is in theory a rationalization that may or may not be unique and as such should not be viewed as unduly limiting with respect to the validity and scope of the claims.

The first step of this proposed mechanism involves the adsorption of the methyl benzoate on the alumina surface indicated as (S) in reaction (1) below. The role of the alumina as a catalyst is consistent with the observation that methyl benzoate is thermally stable at the reaction conditions in the absence of alumina. Adsorption of methyl benzoate on alumina would accentuate the electropositive character of the carbonyl carbon. This would facilitate an intramolecular hydride transfer from the methyl group, resulting in the elimination of a molecule of formaldehyde. The adsorbed benzaldehyde species (I) can undergo three reactions; desorption to give benzaldehyde (2), decomposition to benzene and carbon monoxide (3), and reaction with benzaldehyde to give benzyl benzoate (4). Adsorbed benzyl benzoate species (II) can react with benzyl benzoate to give dibenzyl ether and adsorbed benzoic anhydride (6). Toluene and benzaldehyde are derived from the decomposition of dibenzyl ether (7), whereas adsorbed benzoic anhydride decomposes to benzene, carbon monoxide, and carbon dioxide (8). The thermal formation of benzoic anhydride and dibenzyl ether from benzyl benzoate, followed by the decomposition of dibenzyl ether to benzaldehyde and toluene, is well established in chemical literature. When benzyl benzoate was used as the sole reactant under the reaction condition of our process it was readily decomposed to toluene, benzene and benzaldehyde consistent with the proposed mechanism. The finding of only trace quantities of formaldehyde and the presence of dimethyl ether in the gaseous products of this process is the only experimental evidence inconsistent with the proposed mechanism. However, we have established that formaldehyde at 450°C in the presence of alumina decomposes to give carbon monoxide and dimethyl ether as major products.

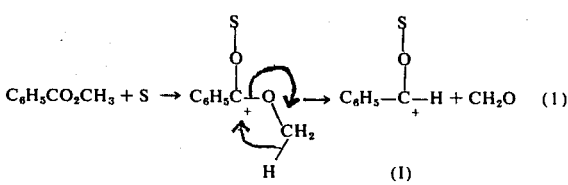

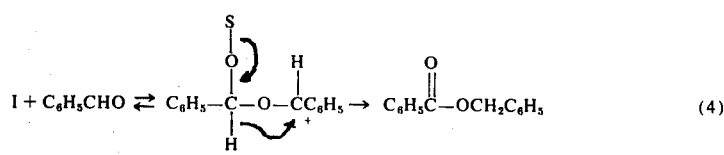

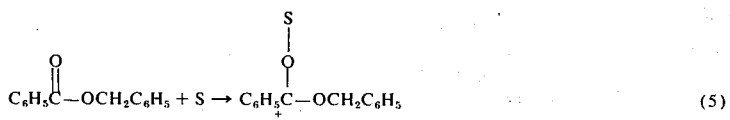

(5)

(II)

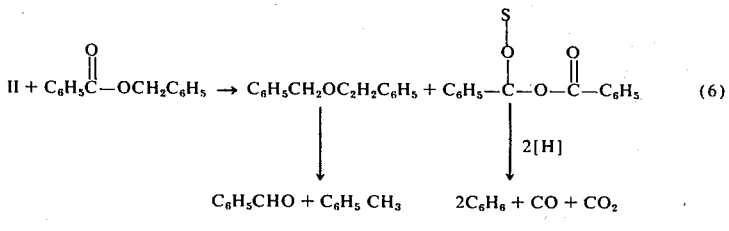

(6)

$$C_6H_5CHO + C_6H_5 CH_3 \qquad 2C_6H_6 + CO + CO_2$$

(7)  (8)

The acceptable aromatic esters which are to be reduced by the vapor-phase reaction of our invention include any of the well-known aromatic hydrocarbons moieties such as phenyl, naphthyl, biphenyl and their substituted counterparts wherein at least one carboxyl group involved in the ester linkage is bonded directly to the aromatic ring. The substituted aromatic moieties should be selected such as to minimize the basicity of the reactant. Thus halo, alkyl, hydroxyl and carboxyl substituted aromatics are operative. An amino substituted aromatic ring is less desirable. Similarly, heterocyclic aromatic rings with enhanced basicity such as those based on a pyridine structure are inoperative. Increased basicity tends to lead to complete decarboxylation to the aromatic product rather than the desired aldehyde. Decarboxylation also tends to occur if the reaction condition is too strenuous. Thus increased residence times and temperatures in excess of 500°C will favor the formation of the decarbomethoxylated aromatic product at the expense of the aldehyde. Hence, the reaction is less practical for synthesis of a dialdehyde from the diester. The most preferred aromatic moiety is the phenyl group.

The alcohol portion of the aromatic ester should be an alkyl group which has no β-hydrogens. This would include the methyl group, isopentyl group and the like. The methyl ester is preferred. The presence of a β-hydrogen permits an alternate mechanism for decomposition. Under the reaction conditions of this process an ester having a β-hydrogen will undergo thermal elimination or pyrolysis wherein the β-hydrogen is transferred to the carbonyl oxygen of the ester linkage and subsequent breaking of chemical bonds yields the aromatic acid and an olefin as products. Thus, in the case of ethyl, cyclohexyl, and tert-butyl benzoate the thermal elimination competed with the reduction reaction to such an extent that no aldehyde product was formed.

The preferred aromatic esters include methyl benzoate and substituted methyl benzoates such as: mono-, di-, and tri-halo substituted methyl benzoate wherein the halogen is fluorine, chlorine or bromine; monoalkyl substituted methyl benzoate wherein the alkyl group is a primary or secondary alkyl group having from 1 to 5 carbon atoms; an alkoxy substituted methyl benzoate having from 1 to 5 carbon atoms; alkylthio substituted methyl benzoate having from 1 to 5 carbon atoms; aryloxy substituted methyl benzoate of up to 12 carbon atoms; cyano substituted methyl benzoate and meta- and para-nitro substituted methyl benzoate.

The acceptable catalysts for our process are derived from aluminum oxide and are commonly known as alumina catalysts. This includes acidic alumina, basic alumina as well as combinations of alumina and other transition metals such as chromia-alumina. These catalysts are readily available in a variety of physical forms and are well known and well documented in literature. A calcined acidic alumina is preferred.

The reaction of this invention can be operated in either a batch mode or a continuous flow system. A flow system is preferred since catalyst contact times as low as 3 seconds are operative while very little advantage is achieved with residence times in excess of 100 seconds. The reaction system should be maintained between 400° and 500°C; preferably, from 440° to 460°C. Below 400°C the percent conversion decreases, apparently because the esters tend to be stable even in the presence of alumina, whereas above 500°C the selectivity of the aldehyde decreases with an increase in the other aromatic products. The reaction vessel can be constructed from a variety of material which are known to be stable at the desired temperatures. In the preferred continuous flow method a purge of inert gas such as dry nitrogen can be used to sweep the ester reactant through the fixed bed of alumina. Advantageously, the calcined alumina catalyst can be saturated with reactant prior to placing it in the reactor in order to reduce the time required to reach steady state reaction conditions.

Having thus described the invention the following examples are presented to illustrate the invention and as such should not be considered unduly limiting. The first eight examples are intended to illustrate the preferred embodiments, and the subsequent three examples illustrate inoperative reactants.

EXAMPLE I to IV

A series of four vapor-phase reactions involving the conversion of methyl benzoate to benzaldehyde as the major product using γ-alumina as a catalyst, were performed at varying reaction conditions. In each case powdered alumina commercially sold as Kaiser 201 γ-alumina was compressed into ⅛ inch pills and calcined for three hours at 538°C. The pills of γ-alumina were immersed in liquid methyl benzoate at 22°C for 2 hours before being placed in a one inch ID Vycor tube reactor. The temperature of the Vycor tube was gradually raised to the desired reaction temperature by the use of an electric furnace. A purge of dry pure nitrogen gas was maintained at a flow rate of 100 cc/minute during preliminary warm-up. After the desired reaction temperature was reached the nitrogen flow rate was cut back to 20 cc/minute. Methyl benzoate was then fed into the reactor through a syringe whose needle fitted through a rubber septum in a glass adaptor connected to the Vycor tube. The syringe was pumped by an infusion pump (Harvard Apparatus Co., Dover, Mass., compact infusion pump, Model 974) at a rate sufficient to give the desired space velocity. The vapors from the reaction were condensed at dry-ice temperatures. Fractions of the condensate were taken at one hour intervals and analyzed by gas chromatography. The noncondensable gases were analyzed by mass spectrometry. A summary of the reaction conditions and data are presented in TABLE I.

TABLE I

| EXAMPLE Reaction Conditions: | I | II | III | IV |
|---|---|---|---|---|
| Temperature °C | 400 | 450 | 450 | 500 |
| Weight Hourly Space Velocity based on methyl benzoate only | .35 | .33 | 1.32 | .95 |
| Time on Stream Hr. | 3.0 | 3.0 | 3.0 | 3.0 |
| Contact Time Sec. | 18 | 17 | 3 | 5 |
| Percent Conversion | 12 | 39 | 21 | 42 |
| Product | Selectivity, Mole % | | | |
| Benzaldehyde | 10 | 37 | 25 | 32 |
| Benzene | 5 | 22 | 14 | 29 |
| Toluene | — | 4 | 1 | 6 |
| Benzyl Benzoate | 2 | 8 | 4 | 4 |

The gaseous products consisted of carbon monoxide, carbon dioxide, dimethyl ether, methane, hydrogen and a trace of formaldehyde. A considerable amount of material remained adsorbed on the alumina catalyst.

EXAMPLE V to VIII

A series of four reactions involving substituted methyl benzoates were performed in a manner analogous to EXAMPLES I to IV, duplicating the reaction conditions of EXAMPLE II. EXAMPLES V and VI were meta- and para-methyl-substituted methyl benzoate; EXAMPLES VII and VIII were meta- and ortho-chloro-substituted methyl benzoate. As seen in TABLE II, conversion and selectivities varied somewhat, but all reactions produced stereospecifically analogous substituted products.

TABLE II

| EXAMPLE Substituted Reactant | V | VI | VII | VIII |
|---|---|---|---|---|
| $CH_3CO_2C_6H_4$—X | X=m-$CH_3$ | X=p-$CH_3$ | X=m-Cl | X=o-Cl |
| Percent Conversion | 27 | 24 | 20 | 57 |
| Products: | Selectivity, Mole % | | | |
| OHC$C_6H_4$—X | 30 | 20 | 31 | 13 |
| $C_6H_5$—X | 26 | 15 | 20 | 53 |
| $CH_3C_6H_5$—X | 7 | 2 | 2 | 2 |

(Weight Hourly Space velocity =.34; Kaiser 201 γ-aluina; 450°C.)

EXAMPLES IX to XI

In comparison to the previous eight examples, three benzoate esters containing β-hydrogens were passed over alumina under the reaction condition of our invention. The three reactants selected were ethyl benzoate, cyclohexyl benzoate and tert-butyl benzoate. In each case thermal elimination competed with the desired hydrogen abstraction mechanism to such an extent the products were benzoic acid and the corresponding olefin. No aldehyde product was formed.

We claim:

1. A process for converting an alkyl ester of an aromatic carboxylic acid to an aromatic aldehyde by contacting said aromatic ester in the vapor phase with alumina from about 400° to 500°C for about 3 to 100 seconds wherein the aromatic moiety of said ester is selected from the group consisting of phenyl, naphthyl and biphenyl moieties, wherein said aromatic moieties are optionally substituted with substituents selected from the group consisting of halo, alkyl, hydroxyl, carboxyl, amino, alkoxy, alkylthio, aryloxy, cyano, and nitro radicals, the said alkyl moiety of said ester is unsubstituted and is free of β-hydrogens.

2. A process of claim 1 wherein said aromatic ester is selected from the group consisting of methyl benzoate; mono-, di-, and tri-halo substituted methyl benzoate wherein the halogen is fluorine, chlorine or bromine; mono-alkyl substituted methyl benzoate where the alkyl group is a primary or secondary alkyl group having from 1 to 5 carbon atoms; an alkoxy substituted methyl benzoate having from 1 to 5 carbon atoms; alkylthio substituted methyl benzoate having from 1 to 5 carbon atoms; aryloxy substituted methyl benzoate of up to 12 carbon atoms; cyano substituted methyl benzoate and meta- and para-nitro substituted methyl benzoate.

3. A process of claim 1 wherein said aromatic ester is an aromatic methyl ester.

4. A process of claim 3 wherein said aromatic methyl ester is methyl benzoate and said aromatic aldehyde is benzaldehyde.

5. A process of claim 4 wherein benzyl benzoate, benzene and toluene are recovered as additional reaction products.

* * * * *

UNITED STATES PATENT OFFICE
CERTIFICATE OF CORRECTION

PATENT NO. : 3,935,265
DATED : January 27, 1976
INVENTOR(S) : Allen Feinstein, Ellis K. Fields It is certified that error appears in the above-identified patent and that said Letters Patent are hereby corrected as shown below:

Col. 1, line 9, "adlehydes" should read -- aldehydes -- per application page 1, line 11.

Col. 3, line 6, "$-H_5\overset{\overset{O}{|}}{\underset{+}{C}}-$" should read -- $-H_5\overset{\overset{O}{|}}{\underset{+}{C}}-$ -- per application page 5, line 5.

Col. 3, line 12, "$-OC_2H_2-$" should read -- $-OCH_2-$ -- per application page 5, line 7.

Col. 6, line 9, "-aluina;" should read -- -alumina; -- per application page 10, line 7.

Signed and Sealed this
first Day of June 1976

[SEAL]

Attest:

RUTH C. MASON
Attesting Officer

C. MARSHALL DANN
Commissioner of Patents and Trademarks